United States Patent [19]

Marsoner et al.

[11] Patent Number: 4,704,893
[45] Date of Patent: Nov. 10, 1987

[54] DEVICE FOR EQUILIBRATING A LIQUID REAGENT

[75] Inventors: Hermann Marsoner, Steinberg; Gerald Kirchmayer; Helmut List, both of Graz, all of Austria

[73] Assignee: AVL AG, Schaffhausen, Switzerland

[21] Appl. No.: 903,199

[22] Filed: Sep. 3, 1986

[30] Foreign Application Priority Data

Dec. 17, 1985 [AT] Austria .................................. 3648/85

[51] Int. Cl.⁴ .............................................. G01N 1/22
[52] U.S. Cl. ................................... 73/1 G; 210/321.69
[58] Field of Search .............. 73/1 G, 863.11, 863.21, 73/863.23, 19; 55/158, 461; 210/433.2, 321.1, 321.5

[56] References Cited

U.S. PATENT DOCUMENTS

| | | | |
|---|---|---|---|
| 3,438,241 | 4/1969 | McKinley, Jr. | 73/19 |
| 3,449,245 | 6/1969 | Johnson et al. | 210/321.1 |
| 3,521,865 | 7/1970 | Kertzman | 73/1 G |
| 3,614,855 | 10/1971 | Van Luik, Jr. | 73/1 G |
| 3,824,836 | 7/1974 | Lyshkow | 73/1 G |
| 4,036,915 | 7/1977 | Lucero et al. | 73/1 G |
| 4,321,908 | 3/1982 | Reed | 237/80 |

FOREIGN PATENT DOCUMENTS 3222617 1/1983 Fed. Rep. of Germany .

*Primary Examiner*—Stewart J. Levy
*Assistant Examiner*—Robert R. Raevis
*Attorney, Agent, or Firm*—Watson, Cole, Grindle & Watson

[57] ABSTRACT

A device for equilibrating small quantities of a liquid reagent or a test solution with a gas-containing liquid or a gas in which at least part of the passage of the reagent leads through a hollow space that is separated by a permeable wall from a gas chamber which is closed, except for an inlet and an outlet opening, and which may be charged with the gas or gas-containing liquid. In order to ensure good mixing of the test liquid during equilibration, the hollow space carrying the liquid is configured as a tube or hose with one or more helical sections inside the gas chamber whose walls are permeable to the gas.

2 Claims, 4 Drawing Figures

DEVICE FOR EQUILIBRATING A LIQUID REAGENT

BACKGROUND OF THE INVENTION

This invention relates to a device for equilibrating small quantities of a liquid reagent or a test solution with a gas-containing liquid or a gas in which at least part of the passage of the reagent leads through a hollow space that is separated by a permeable wall from a gas chamber which, apart from an inlet and an outlet opening, is closed and may be charged with the gas or gas-containing liquid.

Equilibration of a liquid with a gas or of two liquids with one another regarding the content of dissolved gases denotes those measures suitable for bringing into contact the two liquids or a liquid and a particular gas in such a way that the partial pressures of all gas components present will reach an equilibrium after a given time.

DESCRIPTION OF THE PRIOR ART

In conventional equilibration equipment the liquid quantity to be equilibrated is agitated rapidly in a closed chamber into which gas may be blown. As a consequence the liquid spreads over a larger area and is allowed to mix thoroughly with the gas blown in, eventually leading to an equilibrium of the partial pressures.

In another group of known equilibration devices the bottom of a vessel holding the sample is made of porous material through which gas may be blown in. Due to the porous bottom the stream of gas is broken up into small bubbles which will rise in the liquid and lead to an equilibrium of the partial gas pressures and the liquid pressure.

The disadvantage of these known devices is that the gas itself must be saturated with water vapour before it is brought into contact with the liquid in order to avoid water losses of the sample. Another drawback is that these techniques are not suitable for use in a continuous flow of the liquid, and that usually mechanical devices are required for agitating the sample. For these reasons the conventional equipment does not permit continuous equilibration of a flowing reagent.

The latter is possible, however, with a different kind of device, i.e., as described by the German laid-open print DE-OS No. 32 22 617, which is similar to the device specified by the invention. This arrangement includes a chamber through which the test solution is passed. This chamber is separated from the gas chamber by a gas-permeable membrane, the gas chamber being located in the same housing as the chamber carrying the reagent. In order to lengthen the path travelled by the liquid the two chambers are provided with ribs, forcing the liquid and the gas to take a meandering path.

This known kind of device is characterized by a comparatively complex design, however. Besides, as the ribs each time necessitate a change of direction by 90 degrees, dead spaces may develop which will slow down the diffusion rate.

SUMMARY OF THE INVENTION

It is an object of the present invention to eliminate the above disadvantages and to propose a device of the aforementioned type which features design simplicity and a rapid diffusion.

According to the invention this is achieved by configuring the hollow space carrying the test liquid or liquid reagent as a tube or hose which is located inside the gas chamber where it has a gas-permeable wall.

This results in a very simple device for equilibrating small amounts of liquids. Outside of the gas chamber the wall of the permeable hose is sealed gas-tight, for instance by applying a suitable coating, or similar measures. It is also possible, however, to add fittings at the inlet and outlet points of the hose into and out of the gas chamber between which the gas-permeable hose is placed.

An enhanced version of the invention provides that the tube or hose has one or more helical sections inside the gas chamber.

As a consequence the liquid flow through the tube or hose will not be purely axial but will also have a transverse component, resulting in a thorough mixing of the liquid and thus an accelerated diffusion.

The length of the helical tube or hose located in the gas chamber depends on a number of parameters, such as the diameter of the tube or hose carrying the liquid, the wall thickness and diffusion coefficient of the tube wall for gases concerned, the flow velocity of the liquid, or the solubility of the gases in the liquid, and should be selected accordingly.

A preferred variant of the invention provides that the gas chamber be configured as a helical tube or hose inside of which the tube or hose conveying the test liquid is positioned concentrically.

This will result in a particularly simple design which will enable the volume of the gas chamber to be kept small, thus permitting a rapid exchange of gas in the gas chamber.

This arrangement will permit the continuous equilibration of a flowing liquid. In order to avoid differences in temperature as far as possible, the helical section of the tube or hose carrying the test liquid should be preceded by a heat exchanger by means of which the liquid entering the tube/hose may be adjusted to and maintained at a constant temperature.

The gaseous mixture which is drawn from the gas chamber continuously or discontinuously and consists of the carrier gas supplied and the gas(es) to be determined, is fed to an analyzer in a known manner where the content of the gas to be determined is measured.

DESCRIPTION OF THE DRAWINGS

Following is a more detailed description of the invention as illustrated by the attached drawings, in which.

DETAILED DESCRIPTION OF PREFERRED EMBODIMENTS

Figure 1:
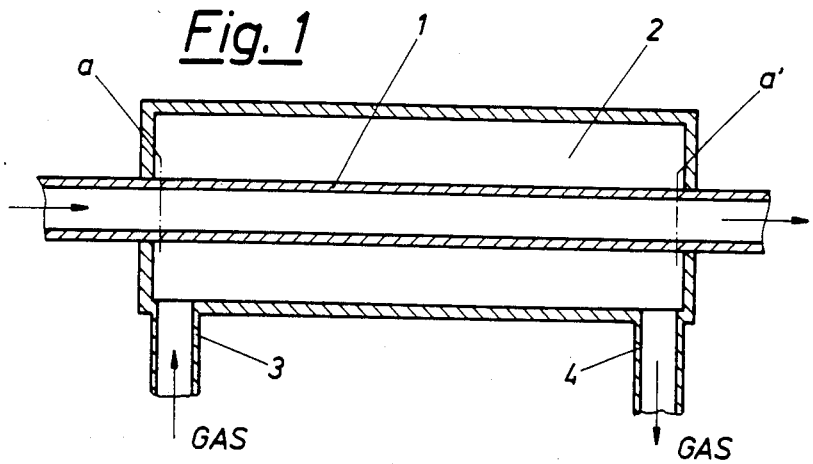
FIG. 1 shows a first embodiment of the invention, FIG. 2 another embodiment, FIG. 3 a velocity profile of the flowing liquid and its flow pattern in a helical tube or hose, and FIG. 4 a schematical view of yet another embodiment of the invention.

In the embodiment shown in FIG. 1 the tube or hose 1 carrying the test liquid is located in a gas chamber 2 which has an inlet 3 and an outlet 4 for a gas or gas-containing liquid. Between points a and a' the wall of the hose 1 is permeable to the gas contained in the gas chamber 2.

While the liquid is passing slowly through the tube or hose 1, e.g., from a to a', gas molecules from the gas chamber 2 and the liquid may balance across the permeable wall of the tube or hose 1, such that at point a' the liquid will have achieved a state of equilibrium with the gas phase.

Figure 2:
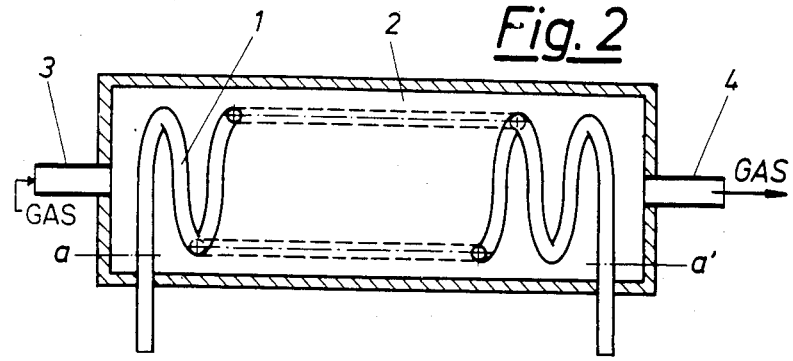

In the embodiment according to FIG. 2 the section of the tube or hose 1 contained in the gas chamber 2 is configured as a helix, leading to a thorough mixing of the liquid and an accelerated diffusion rate. The wall of the helical tube or hose 1 is permeable to the gas which is contained in the gas chamber 2, or rather, which passes through the latter continuously of discontinuously, or to the gas contained in a gassy liquid.

The length of gas-permeable tube/hose between a and a' depends on a number of parameters, e.g., the diameter of the tube/hose, its wall thickness, the diffusion coefficient of the tube/hose material for the gases in question, the flow velocity of the test liquid, and the solubility of the gases in the liquid. The state of equilibrium between gas and liquid resulting from diffusion is reached comparatively slowly, and demands a considerable length of tube/hose with gas-permeable walls. As the tube or hose 1 is arranged in a helix, however, the design may still be kept compact, requiring a minimum of space.

Figure 3:
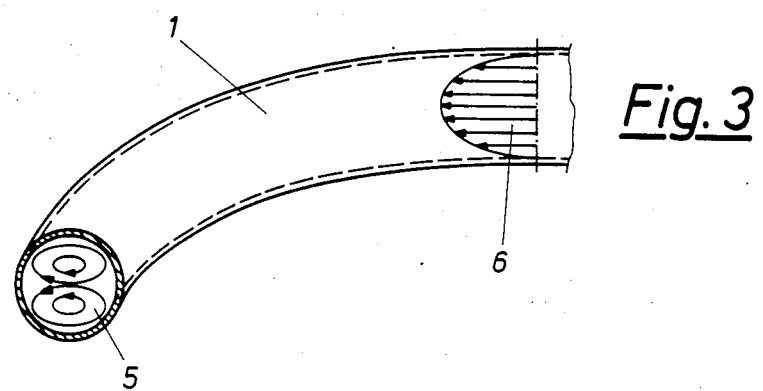

In addition, the helical configuration does not only result in an axial flow of the liquid in the hose but will also lead to transverse flow paths 5, as is shown schematically in FIG. 3.

The velocity profile 6 of the liquid flow in the helical section of the tube or hose 1 which is presented in FIG. 3, results in a good mixing of the test liquid, thus accelerating the diffusion process.

Figure 4:
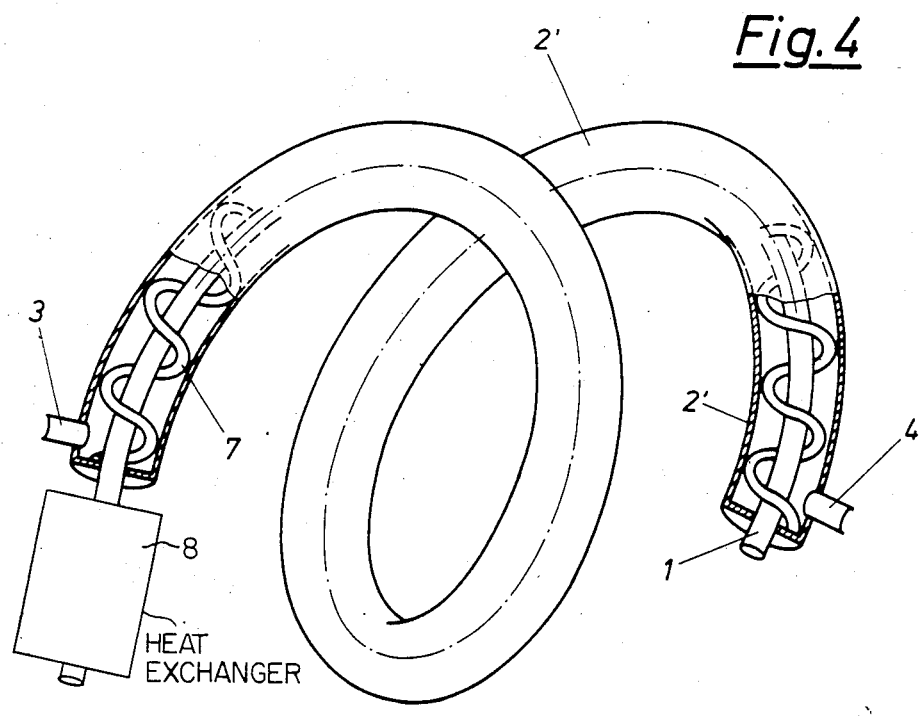

A particularly simple design of a device according to the invention is presented in FIG. 4. In this instance a gas-permeable section of the tube 1 is surrounded by another helical tube or hose 2' acting as the gas chamber whose ends are closed with the exception of an inlet 3 and an outlet 4.

The tube or hose 1 is centered by means of a flexible coil 7 inside the hose 2', the latter being made of a largely non-permeable material.

This kind of arrangement is achieved simply by centering the tube or hose 1 by means of the flexible coil 7 in the nonpermeable hose 2', and by jointly forming the two hoses 1, 2' into a helix, thereby achieving a transverse flow inside hose 1, which will improve mixing of the liquid.

Another advantage of this embodiment is that the gas chamber formed by hose 2' has only a very small volume, which will permit a rapid gas exchange in this chamber if the composition of the equilibration gas has to be altered, as is required in certain applications.

A heat exchanger 8 is preferably placed in front of the helical section of tube 1 such that the interaction of the test liquid with the equilibration gas will always occur at a controlled (constant) temperature, even in case of a continuous flow of the test liquid.

The gaseous mixture drawn from the gas chamber 2 or the hose 2' via the outlet 4 is fed to a gas content analyzer, not shown in this drawing, which will measure the content of the gases to be determined.

We claim:

1. A device for equilibrating small quantities of a liquid reagent with a gas-containing liquid or a gas, said device comprising
    first tube means which extends helically in space, said first tube means providing an elongated gas chamber therein and including an inlet means for enabling said gas-containing liquid or gas to be supplied into said gas chamber and outlet means for enabling said gas-containing liquid or gas to be removed from said gas chamber,
    a second tube means which extends into, continuously concentrically within, and out of said first tube means, said second tube means being used to convey said liquid reagent through said gas chamber, at least a portion of said second tube means which is located within said first tube means being permeable so that the partial pressures of said gas-containing liquid or gas in said gas chamber outside said second tube means will equilibrate with said liquid reagent inside said second tube means, and
    a flexible coil located within said first tube means and helically wrapped around the second tube means to center said second tube means within said first tube means.

2. A device according to claim 1, including a heat exchanger associated with said second tube means to control the temperature of the liquid reagent within said second tube means before passage into said first tube means.

* * * * *